US006503955B1

(12) United States Patent
Dobrozsi et al.

(10) Patent No.: US 6,503,955 B1
(45) Date of Patent: Jan. 7, 2003

(54) POURABLE LIQUID VEHICLES

(75) Inventors: Douglas Joseph Dobrozsi, Loveland, OH (US); Jerry William Hayes, II, Cincinnati, OH (US); Bjorn Olof Lindman, Lund (SE); Rouja Hristova Ivanova, Ilmenau (DE); Paschalis Alexandridis, East Amherst, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/658,813

(22) Filed: Sep. 11, 2000

Related U.S. Application Data
(60) Provisional application No. 60/153,260, filed on Sep. 11, 1999.

(51) Int. Cl.$^7$ .............................. A61K 47/32; A61K 9/14
(52) U.S. Cl. ..................... 514/772.4; 424/485; 424/486
(58) Field of Search ..................... 424/426, 78, 177, 424/485, 486; 514/772.4

(56) References Cited

U.S. PATENT DOCUMENTS

| | | | |
|---|---|---|---|
| 4,100,271 A | 7/1978 | Krezanoski | 424/78 |
| 4,188,373 A | 2/1980 | Krezanoski | 424/78 |
| 4,474,752 A | 10/1984 | Haslam et al. | 424/78 |
| 4,478,822 A | 10/1984 | Haslam et al. | 424/78 |
| 4,511,563 A | 4/1985 | Schmolka | 514/162 |
| 4,810,503 A | 3/1989 | Carson et al. | 424/76.3 |
| 4,849,418 A | 7/1989 | Lohner et al. | 514/163 |
| 4,911,926 A | 3/1990 | Henry et al. | 424/426 |
| 5,030,448 A | 7/1991 | Hunter | 424/83 |
| 5,071,644 A | 12/1991 | Viegas et al. | 514/772.7 |
| 5,135,751 A | 8/1992 | Henry et al. | 424/426 |
| 5,143,731 A | 9/1992 | Viegas et al. | 424/486 |
| 5,256,396 A | 10/1993 | Piechota, Jr. | 424/49 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,318,780 A | 6/1994 | Viegas et al. | 424/427 |
| 5,346,703 A | 9/1994 | Viegas et al. | 424/486 |
| 5,366,735 A | 11/1994 | Henry | 424/426 |
| 5,527,832 A | 6/1996 | Chi et al. | 514/772.4 |
| 5,587,175 A | 12/1996 | Viegas et al. | 424/427 |
| 5,681,576 A | * 10/1997 | Henry | 424/426 |

FOREIGN PATENT DOCUMENTS

| | | | | |
|---|---|---|---|---|
| EP | 0 211 601 | | 2/1987 | .......... A61K/37/36 |
| EP | 0 439 335 A1 | | 7/1991 | ............ A61K/7/16 |
| WO | WO97/21441 | | 6/1997 | .......... A61K/31/77 |

OTHER PUBLICATIONS

Salomonowitz et al., "Hydrophilic–Lipophilic Balance as Predictor of Mucus Coating with Barium Sulfate" *Gastrointest Radio*, vol. 11, pp. 93–96 (1986).

Chen–Chow et al., "In Vitro Release of Lidocaine From Pluronic F–127 Gels", *International Journal of Pharmaceutics*, vol. 8, pp. 89–99 (1981).
Nurnberg et al., "Poloxamere–was ist das? Eigenschaften und Anwendungsmoglichkeiten", *Deutsche Apotheker Zeitung*, vol. 129, No. 41, pp. 2183–2187, (1989).
Reeve, "The Poloxamers: Their Chemistry and Medical Applications", *Handbook of Biodegreadable Polymers*, Editors: A. J. Domb, J. Kost and D. M. Wiseman, Harwood Acaemic Publishers, Chapter 12, pp. 231–249.
Juhasz et al., "Adhesion of Ploxamer 407 Formulations on Dog Ileal in Vitro", *Eur J Pharm Biopharm*, vol. 37, No. 4, pp. 262–265, (1991).
Pandit et al., "Cosolvent Effects on the Gel Formation and Gel Melting Transitions of Pluronic F127 Gels", *Pharmaceutical Development and Technology*, vol. 2, No. 2, pp. 181–184, (1997).
Gilbert et al., "Drug release from Pluronic F–127 gels", *International Journal of Pharmaceutics*, vol. 32, pp. 223–228, (1986).
Lenaerts et al., "Temperature–dependent rheological behavior of Pluronic F–127 aqueous solutions" *International Journal of Pharmaceutics*, vol. 39, pp. 121–127, (1987).
Suh et al., "Pharmacokinetic and Local Tissue Disposition Studies of Naproxen Following Topical and Systemic Administration in Dogs and Rats", *Biopharmaceutics & Drug Disposition*, vol. 18, No. 7, pp. 623–633, (1997).
Cappel et al., "Effect of nonionic surfactants on transdermal drug delivery: II. Poloxamer and poloxamine surfactants", *International Journal of Pharmaceutics*, vol. 69, pp. 155–167, (1991).
Viegas et al., "Osmotic behavior of poloxamer 407 and other non–ionic surfactants in aqueous solutions" *International Journal of Pharmaceutics*, vol. 160, pp. 157–162, (1998).
Lu et al., "Diffusion studies of methotrexate in Carbopol and Poloxamer gels", *International Journal of Pharmaceutics*, vol. 160, pp. 1–9, (1998).
Jewell et al., "Pharmacokinetics of RheothRx Injection in Healthy Male Volunteers", *Journal of Pharmaceutical Sciences*, vol. 7, (1997).
Edsman et al., "Rheological evaluation of poloxamer as an in situ gel for ophthalmic use", *European Journal of Pharmaceutical Sciences*, vol. 6, pp. 105–112, (1998).

(List continued on next page.)

*Primary Examiner*—Thurman K. Page
*Assistant Examiner*—Blessing Fubara
(74) *Attorney, Agent, or Firm*—Joan B. Cunningham; John M. Howell; Karen F. Clark

(57) ABSTRACT

The present invention covers pourable liquid vehicles that can be combined with compositions, materials and substances. Among the benefits of such pourable liquid vehicles is the compositions are retained on the moistened surface for a period of time sufficient to allow compositions, materials and substances to act on said surface, resisting erosion or run-off from additional moisture being applied. Such pourable liquid vehicles have a number of utilities including but not limited to cleaning and treating surfaces of objects as well as biological or living organisms, including living creatures.

27 Claims, No Drawings

OTHER PUBLICATIONS

Bochot et al., "Liposomes Dispersed Within a Thermosensitive Gel: A new Dosage Form for Ocular Delivery of Oligonucleotides", *Pharmaceutical Research*, vol. 15, No. 9, (1998).

Kim et al., "Trials of in situ–gelling and mucoadhesive acetaminophen liquid suppository in human subjects", *International Journal of Pharmaceutics*, vol. 174, pp. 201–207, (1998).

Brown et al., "Thermorheology of polaxamer 407: effect of alcohols and drugs", *J. Pharm. Pharmacol.*, vol. 50, Supplement: pp. 159.

Gaisford et al., "Temperature induced aggregation in aqueous solution of a series of PEO–PPO–PEO copolymers", *International Journal of Pharmaceutics*, vol. 174, pp. 39–46, (1998).

Wang et al., "Kinetics of Sol–to–Gel Transition for Poloxamer Polyols", *Journal of Applied Polymer Science*, vol. 43, pp. 283–292, (1991).

Stratton et al., "Drug Delivery Matrix Containing Native Protein Precipitates Suspended in a Poloxamer Gel", *Journal of Pharmaceutical Sciences*, vol. 86, No. 9, (1997).

* cited by examiner

POURABLE LIQUID VEHICLES

CROSS REFERENCE

This application claims priority under Title 35, United States Code 119(e) from Provisional Application Serial No. 60/153,260, filed Sep. 11, 1999.

TECHNICAL FIELD

Concentrated levels of polyoxyalkylene block copolymers are useful in vehicles incorporated into products that are designed to deliver compositions, materials and substances to moistened surfaces and aqueous environment. Acquiring moisture during use, the vehicle becomes sufficiently transformed from a liquid to a gel-like form that provides a benefit to the user. For example, mucosal surfaces of the body contain sufficient water to allow the pourable liquid vehicle comprising concentrated polyoxyalkylene block copolymers to be effectively delivered to the desired site wherein the accompanying compositions, materials and substances tenaciously adhere to the moistened surfaces and resist dissolution or erosion by water or biological fluid. Such uses include, but are not limited to the delivery of personal health care compositions, formulations and compounds including, but not limited to, pharmaceuticals (OTC and prescription), nutrients and the like.

In the discipline of pharmaceutical compositions there are a wide variety of dosage forms. Examples include tablets, capsules, elixirs, syrups, liquid-filled capsules, suspensions, coated tablets or capsules for administration by mouth; gels, rinses, dentifrices, lozenges, sprays, medicated lollipops, liquid filled capsules for intra-oral administration; gels, suspensions or solutions for intra-ocular or intra-aural administration; suppositories and douches or enemas for intra-rectal or vaginal administration; and creams, ointments, gels, lotions and patches for topical application on the skin and scalp; and liquid suspension or solutions for injection by syringe, nasal gels, solutions, or suspensions for application into the nose with special applications or sprayers.

The majority of these compositions are in the physical form of a fluid having a viscosity ranging from pourable liquids to stiff gels. Pourable liquids are often preferred since they are in the best form to be administered. For example, only liquids, or perhaps low viscosity gels, can be injected through a syringe, or poured from a bottle into a medicine cup, or drawn up into a syringe or medicine dropper, or squeezed from a dropper bottle into the eye or ear, or atomized into the nasal cavities. In addition to the compatibility with pharmaceutical administration devices and with the mode of introduction into the body, it is often desirable for the composition to easily spread after application without the aid of manual action or devices. The eye drop compositions, for example, need to spread over the surface of the eye, as do swallowed liquids intended to coat the throat, esophagus, or stomach. This is similarly true of rectal enemas or vaginal douche compositions.

In many cases, however, pharmaceutical dosage forms in form of pourable liquids are not necessarily desirable since once administered, such pourable liquids are easily removed from the intended treatment site. In such circumstances the therapeutic advantage of the composition may be significantly diminished or even lost completely. It is appropriate, therefore, to surmise that for the purpose of being retained at the targeted site, it may be desirable for a particular pharmaceutical composition to be more viscous, even in the form of a gel that is not readily flowable. It is, however, difficult or even impossible to administer such a viscous composition to its intended site to do the most good. For example, serious injury could occur when attempting to spread a gel on the surface of one's eye using a finger or more elaborate applicators. More problematic is coating the stomach lining, as this site is simply not accessible using simple self-administer applicators.

There is, therefore, a need for pharmaceutical compositions that are "smart"; that is, capable of being administered in a pourable liquid that are converted or transformed after administration into a vehicle having sufficient viscosity to essentially remain at the targeted site. Such compositions require a built-in chemical or physical triggering mechanism(s) that respond to conditions after application in or on a surface including the body.

BACKGROUND OF THE INVENTION

Attempts to develop such compositions have been ongoing for a significant period of time. Examples of such compositions include intra-ocular dosage forms as disclosed in Edsman, K., Carlfors, J., Petersson, R., *Rheological Evaluation of Poloxamer as an In Situ Gel for Ophthalmic Use*, European Journal of Pharmaceutics Vol. 6 pp.105–112 (1998) herein incorporated by reference. Compositions such as these are broadly described as primarily aqueous solutions of block co-polymer surfactants, other wise referred to as "poloxamers", that are commonly known in the art. When formulated in water as somewhat concentrated solutions, or with water and co-solvents, the poloxamer solution remains as a pourable liquid. The most commonly reported example of this type of system consists of poloxamer 407 at concentrations ranging from about 10% to 35% by weight of the composition in water. These compositions are administered at room temperature as liquids. They form a gel upon reaching body temperature. The trigger for converting these compositions to a gel, therefore, is body heat.

In situ gelation of pharmaceutical compositions based on poloxamer that are biologically triggered are known in the art. For example Kim, C. K., Lee, S. W., Choi, H. G., Lee, M. K., Gao, Z. G., Kim, I. S., and Park, K. M.: *Trials of In Situ Gelling and Mucoadhesive Acetaminophen Liquid Suppository in Human Subjects*, International Journal of Pharmaceutics vol. 174, pp. 201–207 (1998) incorporated herein by reference. Kim et al. discloses liquid suppositories for enhancing absorption of the pain and fever relieving drug acetaminophen.

U.S. Pat. No. 5,256,396, issued Oct. 26, 1993, to Colgate Palmolive Company, incorporated herein by reference, describes similar compositions containing poloxamer 407 and water at specified concentrations. Other products utilizing bio-triggers include those comprising poloxamer 407 at ranges preferably 12% to 17%. When combined with pharmaceutically active agents, these compositions are injected into the gingival space between the root of a tooth and the gum.

Poloxamers represent a large family of polymers that vary in molecular weight as well as in the percentage or portion of the block copolymer that is considered hydrophobic. Compositions comprising other poloxamers from this family having similar liquid/gelling characteristics are somewhat predictable, lacking only in the understanding of the required concentration of poloxamer. While there is a large number of uses for such compositions, they all rely on the same general mechanism of temperature-induced gelation of aqueous poloxamer dispersions. Compositions known in the art are found to be inadequate, however, as the gel structure readily dissolves in aqueous environments.

SUMMARY OF THE INVENTION

The present invention covers pourable liquid vehicles used to deliver compositions, materials and substances to moistened surfaces and aqueous environments. The benefits of compositions formulated with such pourable liquid vehicles include retention of the compositions, materials and substances on the moistened surface. This in turn allow for effective delivery of a desired composition, material and substance in the vehicle that acts on targeted surface, resisting erosion or run-off even in an aqueous environment. Such pourable liquid vehicles have a number of utilities for delivery of all kinds of materials including but not limited to cleaning and treating surfaces of objects as well as biological or living organisms, including living creatures.

Another object of this invention is to utilize such pourable liquid vehicles to deliver health care compositions and materials and substances to living creatures, particularly mammals, and most particularly humans. Even another object of the present invention is to develop a method for effective delivery of health care compositions, materials and substances.

DETAILED DESCRIPTION OF THE INVENTION

Definitions

Terms useful herein are defined below. Additionally, terms used in the art, as well as general concepts, are further described in Schramm, *The Language of Colloid and Interface Science*, American Chemical Society, (1993), incorporated herein by reference.

The term "pourable liquid" as used herein means the physical state of the compositions of the present invention prior to formation of a gel.

The term "moistened surface" as used herein means any living or non-living surface having sufficient moisture in or on it to trigger rapid conversion of a pourable liquid to a gel.

The term "in situ gelation" as used herein means the conversion of a pourable liquid to a gel at a designated site or surface.

As used herein, the term "gel" describes the substance resulting from the combination of the pourable liquid and water, or bodily fluid containing mostly water. The gel is sufficiently viscous to remain at the site applied to, or ultimately targeted for, over a period of time sufficient for the compositions, materials and substances in the gel to bring about a desired result at the site they are delivered to.

The term "triggering device" as used herein means a stimulus external to the composition that induces the conversion of a pourable liquid to a gel.

The term "shear" as used herein is the rate of deformation of a fluid when subjected to a mechanical shearing stress. In simple fluid shear, successive layers of fluid move relative to each other such that the displacement of any one layer is proportional to its distance from a reference layer. The relative displacement of any two layers divided by their distance of separation from each other is termed the "shear" or the "shear strain". The rate of change with time of the shear is termed the "shear rate".

A certain applied force is needed to produce deformation in a fluid. For a plane area around some point in the fluid and in the limit of decreasing area the component of deforming forces per unit area that acts parallel to the plane is the "shear stress".

The "viscosity" of a viscous material, also called viscosity index, is defined as the ratio of the shear stress applied into the material, divided by the rate of shear which results. Materials of a higher viscosity have a higher resistance to flow, or to forces which can induce flow, than a lower viscosity material. All viscosities listed herein are at a shear rate of about 50 per second unless otherwise indicated. All of the rheologic characteristics given herein can be measured in a controlled rate or a controlled stress rotational viscometer capable of some operation in a controlled rate mode, for Example Haake RS 150 by Haake GmbH, Karlsruhe, Germany; Carrimed CSL 500 Controlled Stress Rheometer by TA Instruments, New Castle, Delaware; and Rheometric SR5, by Rheometric Scientific, Piscataway, N.J.

Specifically, when subject to constant shearing rate of about 50 per second at normal ambient temperature (approx. 25° C.), the present liquid compositions have a viscosity of less than about 7 pascal seconds, preferably less than about 2 pascal seconds, more preferably less than about 1 pascal seconds.

The value of a composition's triggered viscosity ratio ("T") is useful in determining the degree to which a composition exhibits the above described gelling characteristic. The formula and procedure for determining the triggered viscosity ratio is set forth below.

It is desirable for the compositions of the present invention to exhibit a triggered viscosity ratio of at least about 1.3, preferably at least about 2, more preferably at least about 5, and most preferably at least about 10 wherein the triggered viscosity is defined by the following formula or ratio:

$$T = \eta_g / \eta_f$$

where $\eta_g$=viscosity of the gel and
where $\eta_f$=viscosity of the pourable liquid The pourable liquid vehicle of the present invention must be selected and formulated so that the contacting and mixing said vehicles to a mucosal surface of the body, or with some other fluid in the body, triggers the conversion of the pourable liquid vehicle to a more viscous gel-like mixture. Examples of these fluids are saliva, gastric fluid, intestinal fluid, extracellular fluid present under the skin at the site of a subcutaneous injection, or in muscle tissue at the site of an intramuscular injection, cerebrospinal fluid, vaginal fluid, fluid exudate from an open wound or ulcer, tear fluid, rectal fluid, or any other bodily fluid of an animal which contains in large measure water. In other words, after the pourable liquid vehicle contacts with the bodily fluid, the viscosity of the pourable liquid vehicle becomes greater than the viscosity of either the pourable liquid vehicle itself prior to mixing, or the bodily fluid alone.

The triggered viscosity ratio of a pourable liquid vehicle can be determined by one skilled in the art using appropriate viscosity measuring instruments, and is exemplified by the following method. First, the viscosity of the pourable liquid vehicle ($\eta_f$) is determined in a rheometer using a shear rate of 50 per second at 25° C. For the determination of $\eta_f$, 1 ml of the pourable liquid vehicle is placed onto the plate of a Haake RS 150 rheometer. The temperature is controlled in the range of typical room temperature, about 25° C. A cover is used on the measuring system and a solvent-saturated atmosphere provided to prevent evaporation of water, ethanol, or other volatile components from the sample during the test. A 35 mm diameter parallel plate measuring system is lowered onto the sample, leaving a gap of about 1 millimeter, and an equilibration shearing of approximately 10 per second is applied for 10 seconds. Then, a constant shearing rate of 50 per second is applied for 30 seconds. The viscosity $\eta_f$ is read from the instrument at the 30 second time point.

For the determination of $\eta_g$, two dilutions of the pourable liquid vehicle are made with water. The first dilution is made to contain 75% by weight of the pourable liquid vehicle, and 25% by weight of additional water. The second dilution is made to contain 50% by weight of pourable liquid vehicle and 50% by weight of additional water. The pourable liquid vehicle and water are combined in a vial and a tight seal applied to prevent evaporation of components. The vial contents are mixed in an unusual manner, by repeated centrifugation. This is necessary since some of the combinations are very viscous gels. Specifically, the vials are centrifuged (using for example a Beckman GS-6R centrifuge, available from Beckman Instruments, Palo Alto, Calif.) 20 minutes at 3000 RPM and 25° C. for at least four separate centrifuge runs. After each run the vials are inverted. Additional runs are conducted in the centrifuge to ensure complete mixing. 1 ml of the gelled sample is then loaded onto the plate of the same rheometer used for the measurement of $\eta_f$, except that the temperature is controlled at the normal body temperature of a human, 37° C. An identical rheometer measurement program is used as for determination of $\eta_f$. The triggered viscosity factor for both the 25% and 50% dilution of the sample is calculated from $\eta_f$ and $\eta_g$ as described by the formula above. These two dilutions have been found to be useful for measuring the gelling functionality of the pourable liquid vehicles of the invention in a standardize method, because some of the pourable liquid vehicles may require a greater or lesser amount of water in order to trigger the gelling character. The use of other water dilutions for determination of $\eta_g$, ranging from about 5% up to about 70%, would also be expected to provide a demonstration of the unique, gelling character of the invention, but the dilution which yields a maximal value of T varies depending upon the exact pourable liquid vehicle being tested.

All percentages of the components comprising the invention are herein referred to their weight in the pourable liquid vehicle as a whole.

The present invention is a pourable liquid vehicle comprising:

(a) from about 26% to about 100% polyoxyalkylene block copolymer;

(b) from about 0% to about 70% glycol; and (c) from about 0% to about 50% water;

wherein said vehicle is used to deliver compositions, materials and substances to moistened surfaces and aqueous environments said vehicle has a viscosity value $\eta_f$ less than or equal to 7 pascal-seconds and the value T greater than or equal to about 1.3.

Polyoxyalkylene Block Copolymer

Polyoxyalkylene block copolymers herein referred to as "poloxamers" are nonionic block copolymers of ethylene oxide and propylene oxide corresponding to the following structure:

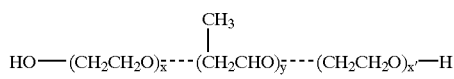

wherein x, y, and x' have a value wherein the pourable liquid vehicle has a viscosity value $\eta_f$ less than or equal to 7 pascal-seconds and the value T greater than or equal to about 1.3. Preferable polyoxyalkylene block copolymers useful in the present invention include wherein x has a value from about 1 to about 130, y has a value from about 1 to about 72, and x' has a value from 0 to about 130, wherein the average molecular weight of said copolymer is from about 3000 to about 15,000. More preferred is wherein x equals 37, y equals 58, and x' equals 37, and the copolymer has an average molecular weight of about 6500. Most preferred is wherein x equals 100, y equals 70, and x' equals 100, and the copolymer has an average molecular weight of about 12,600.

The poly(oxyethylene) segment is hydrophilic and the poly(oxypropylene) segment is hydrophobic. The level of the poloxamers useful in the present invention ranges from about 26% to about 100%, preferably from about 27.8% to about 95%, more preferably 30% to about 90% by weight of the pourable liquid vehicle. In other words, providing the poloxamer has the critical viscosities above, it can be used itself or when combined with other compositions, materials and substances.

A family of poloxamers are available and vary in the number of blocks, the overall average molecular weight, and in the percentage of the molecule which is hydrophilic. A block refers to a single polyoxyethylene or polyoxypropylene segment. Di-block and tri-block polymers have been described. In the case of tri-block copolymers, the blocks can be arranged in the format of one polyoxypropylene block surrounded by 2 polyoxyethylene blocks, that being the most common poloxamer structure, or alternatively as one polyoxyethylene block surrounded by 2 polyoxypropylene blocks, the latter sometimes referred to as a reverse poloxamer. Poloxamers are available under the trade names of Lutrol, Monolan, or Pluronic. The chemical structure, synthesis, and properties have been described [(poly (ethylene oxide)/poly(propylene oxide)] block copolymer surfactants, Paschalis Alexandridis, *Current Opinions in Colloid and Interface Science*, Vol 2, pp. 478–489 (1997) herein incorporated by reference.

For applications in the health care area, compositions embodying the present invention utilize a specific group of pharmaceutically acceptable block copolymers or poloxamers. These poloxamers are selected from the group consisting of Pluronic F127, P105, F108 and mixtures thereof, all available from BASF Corp.

Glycols

In addition to the poloxamers, it is desirable in some of the pourable liquid vehicles of the present invention to combine glycols with the poloxamers for controlling the viscosity of the pourable liquid vehicles, These glycols permit the pourable liquid vehicle to remain pourable while containing very high levels of the poloxamer so that administration is convenient, or so that the composition can readily pass through the bore of a syringe or other dosing apparatus, Additionally, these glycols provide solvent capacity for pharmaceutical actives or other composition components. The level of glycols in the present invention is from 0% to about 70%, preferably from about 10% to about 70% and most preferably from about 7% to about 62% of the pourable liquid vehicle.

Glycols are low molecular weight polyols and are selected from the group consisting of monosaccharides such as glucose (dextrose), fructose (levulose); disaccharides such as sucrose, lactose, maltose, cellobiose and other sugars, ribose, glycerin, sorbitol, xylitol, inositol, propylene glycol, galactose, mannose, xylose, rhamnose, glutaraldehyde, invert sugars, ethanol, honey, mannitol, polyethylene glycol, glycerol and mixtures thereof. Preferred glycols are selected from the group consisting of ethanol, glycerol and propylene glycol, and mixtures thereof. Absolute ethanol is available from Aaper Alcohol & Chemical Co., Shelbyville, Ky.

Water

In addition to the poloxamers, and, or the glycol, it is desirable in some of the pourable liquid vehicles of the present invention to include water. Water is useful at a level from 0% to about 50%, preferably about 1% to about 46%, most preferably from about 2% to about 41% of the pourable liquid vehicle.

Preferred Embodiments

Preferred embodiments of the present invention utilizing the combination of poloxamers, polyols and water include the following:

1. from about 26% to about 65% Pluronic F127, from about 22% to about 38% ethanol and from about 8% to about 45% water.
2. from about 52% to about 60% Pluronic F108, from about 20% to about 25% ethanol and from about 17% to about 27% water.
3. from about 25% to about 50% Pluronic P105, from about 45% to about 65% propylene glycol and from about 5% to about 20% water.
4. from about 37% to about 77% Pluronic P105, from about 12% to about 28% ethanol, and from about 10% to about 45% water
5. from about 26% to about 49% Pluronic F127, from about 2% to about 12% ethanol, from about 30% to about 68% propylene glycol, and from about about 7% to about 40% water.

Materials to be Delivered

As previously stated, the pourable liquid vehicles of the present invention are useful as delivery vehicles for desired compositions, materials and substances that may be dispersed into them. This could range from compositions, materials and substances that are desired to remain on an applied surface for a period of time to deliver a benefit. Examples include antimicrobials for cleansing surfaces including sinks, toilets and shower tile; to body wounds; oral treatment of gingival and buccal tissues as well as teeth surfaces; agricultural uses including elimination of undesirable plants, animals, viruses, bacteria insects, and the like.

The present invention is particularly useful for the delivery of health care compositions, materials, and substances. These materials can range from dietary compositions to promote nutrition or weight loss to pharmacologically effective amounts of agents selected from the group consisting of antibacterial substances, antihistamines, antitussives, antiinflammatories, expectorants/mucolytics, mast cell stabilizers, leukotriene antagonists, methylxanthines, antioxidants, steroids, bronchodilators, antivirals, biologics, analgesics, anesthetics, antiarthritics, antiasthmatics, urinary tract disinfectives, anticoagulants, anticonvulsants, antidepressants, antidiabetics, antineoplastics, antipsychotics, antihypertensives, muscle relaxants, antiprotozoals, and mixtures thereof.

Preferred embodiment of the present invention relates to compositions including pharmaceutically acceptable polyoxyalkylene block copolymer and glycols in combination with a pharmacologically active agent. Suitable classes of agents that can be administered by embodiments of the present invention include:

Antibacterial substances such as β-lactum antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanaranycin, amikacin, sisomicin and tobramycin; nalidixic acids and analogs such as norfloxacin and the antimicrobial combination of fluoroalanine/pentizidone; nitrofarazones, and mixtures thereof.

Antihistamines, including, Hydroxyzine, Pyrilamine, Phenindamine, Dexchlorpheniramine, Clemastine Diphenhydramine, Azelastine, Acrivastine, Levocarbastine, Mequitazine, Astemizole, Ebastine, Loratadine, Cetirizine, Terfenadine, Promethazine, Dimenhydrinate, Meclizine, Tripelennamine, Carbinoxamine, Cyproheptadine, Azatadine, Brompheniramine, Triprolidine, Cyclizine, Thonzylamine, Pheniramine, and mixtures thereof.

Antitussives, including, Hydrocodone, Noscapine, Benzonatate, Diphenhydramine, Chlophedianol, Clobutinol, Fominoben, Glaucine, Pholcodine, Zipeprol, Hydromorphone, Carbetapentane, Caramiphen, Levopropoxyphene, Codeine, Dextromethorphan, and mixtures thereof.

Antiinflammatories preferably Non-Steroidal Antiinflammatories (NSAIDS) including, Ketoprofen, Indoprofen, Indomethacin, Sulindac, Diflunisal, Ketorolac, Piroxicam, Meclofenamate, Benzydamine, Carprofen, Diclofenac, Etodolac, Fenbufen, Fenoprofen, Flurbiprofen, Mefenamic, Nabumetone, Phenylbutazone, Pirprofen, Tolmetin, Ibuprofen, Naproxen, Sodium naproxen, Aspirin, and mixtures thereof.

Expectorants/Mucolytics, including, Ambroxol, Bromhexine, Terpin, Guaifenesin, Potassium iodide, N-Acetylcysteine, and mixtures thereof.

Mast Cell Stabilizers, preferably intranasally, or orally administered mast cell stabilizers, including, Cromolyn, Oxatamide, Ketotifen, Lodoxamide, Nedocromil, and mixtures thereof.

Leukotriene Antagonists, including, Zileuton and others.

Methylxanthines, including, Caffeine, Theophylline, Enprofylline, Pentoxifylline, Aminophylline, Dyphylline, and mixtures thereof.

Antioxidants or radical inhibitors, including, Ascorbic acid, Tocopherol, Pycnogenol, and mixtures thereof.

Steroids, preferably intranasally administered steroids, including, Beclomethasone, Fluticasone, Budesonide, Mometasone, Triamcinolone, Dexamethasone, Flunisolide, Prednisone, Hydrocortisone and mixtures thereof.

Bronchodilators, preferably for inhalation, including, Albuterol, Epinephrine, Ephedrine, Metaproterenol, Terbutaline, Isoetharine, Terbutaline, Isoetharine, Pirbuterol, Bitolterol, Fenoterol, Rimeterol, Ipratroprium, and mixtures thereof.

Antivirals, including, Amantadine, Rimantadine, Enviroxime, Nonoxinols, Acyclovir, Alpha-Interferon, Beta-Interferon, and mixtures thereof.

Biologics, including, cytokine and celladhesion molecule inhibitors, ICAM antagonists, interleukin agonists or antagonists, hormones, polypeptides, amino acids, nucleotides, antibodies, and mixtures thereof.

Analgesics such as aspirin, acetaminophen, diflunisal, and mixtures thereof. Anesthetics such as lidocaine, procaine, benzocaine, xylocaine, and mixtures thereof.

Antiarthritics such as phenylbutazone, indomethacin, sulindac, dexamethasone, ibuprofen, allopurinol, oxyphenbutazone, probenecid, and mixtures thereof.

Antiasthma drugs such as theophylline, ephedrine, beclomethasone dipropionate, epinephrine, and mixtures thereof.

Urinary tract disinfectives such as sulfamethoxazole, trimethoprim, nitrofurantoin, norfloxacin, and mixtures thereof.

Anticoagulants such as heparin, bishydroxycoumarin, warfarin, and mixtures thereof.

Anticonvulsants such as diphenylhydantoin, diazepam, and mixtures thereof.

Antidepressants such as amitriptyline, chlordiazepoxide, perphenazine, protriptyline, imipramine, doxepin, and mixtures thereof.

Antidiabetics such as insulin, tolbutamide, tolazamide, acetohexamide, chlorpropamide, and mixtures thereof.

Antineoplastics such as adriamycin, fluorouracil, methotrexate, asparaginase, and mixtures thereof.

Antipsychotics such as prochlorperazine, lithium carbonate, lithium citrate, thioridazine, molindone, fluphenazine, trfluoperazine, perphenazine, amitriptyline, triflupromazine, and mixtures thereof.

Antihypertensive such as spironolactone, methyldopa, hydralazine, clonidine, chlorothiazide, deserpidine, timolol, propranolol, metoprolol, prazosin hydrochloride, reserpine, and mixtures thereof.

Muscle relaxants such as melphalan, dantrolene, cyclobenzaprine, methocarbamol, diazepam, and mixtures thereof.

Antiprotozoals such as chloramphenicol, chloroquine, trimethoprim, sulfamethoxazole, and mixtures thereof.

For treatment of vaginal and urethral conditions requiring antifungal, amoebicidal, trichomonoacidal agents or antiprotozoals, the following agents can be used: polyoxyethylene nonylphenol, alkylaryl sulfonate, oxyquinoline sulfate, miconazole nitrate, sulfanilamide, candicidin, sulfisoxazole, nystatin, clotrimazole, metronidazole and mixtures thereof; antiprotozoals such as chloramphenicol, chloroquine, trimethoprim, sulfamethoxazole and mixtures thereof; antiviral effective compounds such as acyclovir and interferon. Spermicidals can be used such as nonoxynal.

EXAMPLES

Example I

Composition for the Treatment of Cough

| Component | % (w/w) |
|---|---|
| Dextromethorphan Base | 1.47 |
| Vehicle[1] | 98.18 |
| Sodium Saccharin | 0.3 |
| Monoammonium Glycerizzinate | 0.05 |
| Flavors and Colors | Flavors and Colors |

[1]Vehicle contains (w/w %):
Pluronic F127  55.51%
   (BASF Specialty Chemicals, Mount Olive, N.J.)
Ethanol   26.48%
Water   18.01%

Preparation

Add the dextromethorphan base, sodium saccharin, and monoammonium glycerizzinate into a clean vessel. Add ethanol and then the poloxamer and water. Mix until clear and uniform.

Example II

Composition for the Treatment of Cough and Decongestion

| Component | % (w/w) |
|---|---|
| Dextromethorphan Base | 1.47 |
| Chlorophenarimine Malcate | 0.26 |
| Vehicle[1] | 97.92 |
| Sodium Saccharin | 0.3 |
| Monoammonium Glycerizzinate | 0.05 |
| Flavors and Colors | As Desired |

[1]Vehicle contains (w/w %):
Pluronic F127  55.66%
   (BASF Specialty Chemicals, Mount Olive, N.J.)
Ethanol   26.55%
Water   17.79%

Preparation

Mill and screen the menthol and tienzoocaine to reduce the product particle size. Add the menthol, benzocaine, sodium saccharin, and monoammonium glycerizzinate into a clean vessel. Add eucalyptus oil, ethanol to the vessel. Subsequently add the poloxamer and water to the vessel. Mix until uniform.

Example III

Demulcent Composition for the Treatment of Sore Throat

| Component | % (w/w) |
|---|---|
| Vehicle[1] | 96.845 |
| Menthol | 1.00 |
| Benzocaine | 2.00 |
| Eucalyptus Oil | 0.005 |
| Sodium Saccharin | 0.10 |
| Monoammonium Glycerizzinate | 0.05 |
| Flavors and Colors | As Desired |

[1]Vehicle contains (w/w %):
Pluronic F108  56.79%
   (BASF Specialty Chemicals, Mount Olive, N.J.)
Ethanol   21.69%
Water   21.52%

Preparation

Mill and screen the menthol and benzocaine to reduce the product particle size. Add the menthol, benzocaine, sodium saccharin, and monoammonium glycerizzinate into a clean vessel. Add eucalyptus oil, ethanol to the vessel. Subsequently add the poloxamer and water to the vessel. Mix until uniform.

Example IV

Composition for the Rectal Delivery of Acetaminophen

| Component | % (w/w) |
|---|---|
| Vehicle[1] | 95.0 |
| Acetaminophen | 5.0 |

[1]Vehicle contains (w/w %):
Pluronic P105  44.21%
   (BASF Specialty Chemicals, Mount Olive, N.J.)
Propylene Glycol  52.63%
Water    3.16%

Preparation

Mill and screen the acetaminophen to reduce the particle size. Add the acetaminophen into a clean vessel. Add propylene glycol to the vessel. Subsequently add the poloxamer and water to the vessel. Mix until uniform.

Example V

Composition for the Topical Delivery of an Analgesic

| Component | % (w/w) |
|---|---|
| Vehicle[1] | 98.0 |
| Ketoprofen | 2.0 |
| Perfumes | As Desired |

[1]Vehicle contains (w/w %):
Pluronic F127  56.12%
             (BASF Specialty Chemicals, Mount Olive, N.J.)
Ethanol       30.61%
Water         13.27%

Preparation

Screen the ketoprofen to reduce the particle size. Add the ketoprofen into a clean vessel. Add ethanol to the vessel. Subsequently add poloxamer and water to the vessel. Mix until uniform.

Example VI

Composition for the Topical Delivery of an Analgesic

| Component | % (w/w) |
|---|---|
| Vehicle[1] | 95.0 |
| Ibuprofen | 5.0 |
| Perfumes | As Desired |

[1]Vehicle contains (w/w %):
Pluronic P105  63.16%
             (BASF Specialty Chemicals, Mount Olive, N.J.)
Ethanol       18.95%
Water         17.89%

Preparation

Screen the ibuprofen to reduce the particle size. Add the ibuprofen into a clean vessel. Add ethanol to the vessel. Subsequently add the poloxamer and water to the vessel. Mix until uniform.

Example VII

Composition for the Delivery of an Oral Antimicrobial

| Component | % (w/w) |
|---|---|
| Vehicle[1] | 98.57 |
| Triclosan Monophosphate | 0.28 |
| Menthol | 1.00 |
| Sodium Saccharin | 0.10 |
| Monoammonium Glycerizzinate | 0.05 |
| Flavors and Colors | As Desired |

[1]Vehicle contains (w/w %):
Pluronic F108  55.80%
             (BASF Specialty Chemicals, Mount Olive, N.J.)
Ethanol       21.30%
Water         22.90%

Preparation

Mill and screen the menthol and triclosan monophosphate to reduce particle size. Add the menthol, triclosan monophophate, sodium saccharin, and monoammonium glycerizzinate into a clean vessel. Add propylene glycol to the vessel. Subsequently add the poloxamer and water to the vessel. Mix until uniform.

Example VIII

Composition for the Intranasal Delivery of a Decongestant

| Component | % (w/w) |
|---|---|
| Vehicle[1] | 99.32 |
| Oxymetazoline HCl | 0.05 |
| Tyloxapol | 0.15 |
| Dibasic Sodium Phosphate | 0.04 |
| Monobasic Potassium Phosphate | 0.13 |
| Benzalkonium Chloride | 0.04 |
| Chlorhexidine Gluconate | 0.26 |
| Disodium EDTA | 0.01 |

[1]Vehicle contains (w/w %):
Pluronic F127  40.27%
             (BASF Specialty Chemicals, Mount Olive, N.J.)
Ethanol       26.18%
Water         33.55%

Preparation

Add the dibasic sodium phosphate, monobasic potassium phosphate, disodium EDTA, benzalkonium chloride and oxymetazoline HCl into a clean vessel. Add tyloxapol, chlorhexidine gluconate, and ethanol to the vessel. Subsequently add, the poloxamer and water to the vessel. Mix until uniform.

Example IX

Composition to Vaginally Deliver Hormonal Replacement Therapy

| Component | % (w/w) |
|---|---|
| Vehicle[1] | 99.99 |
| Beta Estradiol | 0.01 |
| Perfumes | As desired |

[1]Vehicle contains (w/w %):
Pluronic P105     45.00%
                (BASF Specialty Chemicals, Mount Olive, N.J.)
Propylene glycol  48.00%
Water              7.00%

Preparation

Add the beta estradiol and propylene glycol into a clean vessel. Subsequently add the poloxamer and water to the vessel. Mix until uniform.

Example X

Composition for the Rectal Delivery of an Antiemetic

| Component | % (w/w) |
|---|---|
| Vehicle[1] | 99.75 |
| Promethazine HCl | 0.25 |

[1]Vehicle contains 100.0% (w/w %) Pluronic L62 (BASF Specialty Chemicals, Mount Olive, N.J.)

Preparation

Mill and screen the promethazine HCl to reduce particle size. Add the poloxamer and the Promethazine HCl into a clean vessel. Mix until uniform.

Example XI

Composition for the Rectal Delivery of an Antiemetic

| Component | % (w/w) |
|---|---|
| Vehicle[1] | 98.75 |
| Carbomer[2] | 1.00 |
| Promethazine HCl | 0.25 |

[1]Vehicle contains 100.0% (w/w %) Pluronic L62 (BASF Specialty Chemicals, Mount Olive, N.J.)
[2]Carbopol 974 available from B. F. Goodrich Company, Brecksville, Ohio Preparation Mill the promethazine HCl to reduce particle size. Sieve the carbomer and promethazine HCl and add to a clean vessel. Add the poloxamer. Mix until uniform.

Example XII

Composition for the Treatment of Cough

| Component | % (w/w) |
|---|---|
| Dextromethorphan Base | 2.20 |
| Vehicle[1] | 95.15 |
| Sodium Metabisulfite | 0.10 |
| Disodium EDTA | 0.10 |
| Sodium Saccharin | 0.40 |
| Monoammonium Glycerizzinate | 0.15 |
| Acesulfame | 0.50 |
| Flavor | 1.40 |

[1]Vehicle contains (w/w %):
Pluronic F127   33.56%
   (BASF Specialty Chemicals, Mount Olive, N.J.)
Ethanol   10.51%
Water   13.42%
Propylene glycol   42.51%

Preparation

Add propylene glycol and poloxamer to a clean vessel (main mix). While stirring, heat the mixture as appropriate to sufficiently melt the poloxamer. Once a uniform solution is obtained remove from heat source and continue mixing. In a separate vessel (alcohol pre-mix) add alcohol, dextromethorphan base and monoammonium glycerizzinate and mix until uniform. In another vessel (water pre-mix), add water, EDTA, sodium saccharin, acesulfame and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, add desired flavor component and mix until uniform.

The preparation has a viscosity ($\eta_f$) of 0.67 Pascal seconds and a triggered viscosity ratio at a 50% dilution with water of 10.5.

Example XIII

Composition for the Treatment of Cough

| Component | % (w/w) |
|---|---|
| Dextromethorphan Base | 2.20 |
| Vehicle[1] | 95.15 |
| Sodium Metabisulfite | 0.10 |
| Disodium EDTA | 0.10 |
| Sodium Saccharin | 0.40 |
| Monoammonium Glycerizzinate | 0.15 |
| Acesulfame | 0.50 |
| Flavor | 1.40 |

[1]Vehicle contains (w/w %):
Pluronic F127   29.08%
   (BASF Specialty Chemicals, Mount Olive, N.J.)
Ethanol   10.51%
Water   24.61%
Propylene glycol   35.80%

Preparation

Add propylene glycol and poloxamer to a clean vessel (main mix). While stirring, heat the mixture as appropriate to sufficiently melt the poloxamer. Once a uniform solution is obtained remove from heat source and continue mixing. In a separate vessel (alcohol pre-mix) add alcohol, dextromethorphan base and monoammonium glycerizzinate and mix until uniform. In another vessel (water pre-mix), add water, EDTA, sodium saccharin, acesulfame and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, add desired flavor component and mix until uniform.

The preparation has a viscosity ($\eta_f$) of 0.97 Pascal seconds and a triggered viscosity ratio at a 50% dilution with water of 4.95.

Example XIV

Composition for the Treatment of Cough

| Component | % (w/w) |
|---|---|
| Dextromethorphan Base | 2.20 |
| Vehicle[1] | 95.15 |
| Sodium Metabisulfite | 0.10 |
| Disodium EDTA | 0.10 |
| Sodium Saccharin | 0.40 |

-continued

| Component | % (w/w) |
| --- | --- |
| Monoammonium Glycerizzinate | 0.15 |
| Acesulfame | 0.50 |
| Flavor | 1.40 |

[1]Vehicle contains (w/w %):
Pluronic F127  40.27%
  (BASF Specialty Chemicals, Mount Olive, N.J.)
Ethanol  10.51%
Water  13.42%
Propylene glycol  35.80%

Preparation

Add propylene glycol and poloxamer to a clean vessel (main mix). While stirring, heat the mixture as appropriate to sufficiently melt the poloxamer. Once a uniform solution is obtained remove from heat source and continue mixing. In a separate vessel (alcohol pre-mix) add alcohol, dextromethorphan base and monoammonium glycerizzinate and mix until uniform. In another vessel (water pre-mix), add water, EDTA, sodium saccharin, acesulfame and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, add desired flavor component and mix until uniform.

The preparation has a viscosity ($\eta_f$) of 2.14 Pascal seconds and a triggered viscosity ratio at a 50% dilution with water of 6.05.

Example XV

Composition for the Treatment of Cough

| Component | % (w/w) |
| --- | --- |
| Dextromethorphan Base | 2.20 |
| Vehicle[1] | 97.8 |
| Flavors | As desired |

[1]Vehicle contains (w/w %):
Pluraflo 1220  40.90%
  (BASF Specialty Chemicals, Mount Olive, N.J.)
Ethanol  10.22%
Propylene Glycol  46.83%
Anhydrous glycerine  2.05

Preparation

Weigh the dextomethophan into a clean vessel, add the ethanol and begin mixing. Add propylene glycol and mix until uniform and clear. Add Pluraflo and mix. Add glycerin and mix until uniform. Subsequently, add desired flavor component and mix until uniform.

The proportions of poloxamer:glycol in the preparation is 40.90:59.10.

Example XVI

Composition for the Treatment of Otitis

| Component | % (w/w) |
| --- | --- |
| ofloxacin | 0.30 |
| Vehicle[1] | 98.95 |
| Perfume | 0.75 |

[1]Vehicle contains (w/w %):
Pluraflo 1220  45.48%
  (BASF Specialty Chemicals, Mount Olive, N.J.)
Ethanol  5.05%
Propylene Glycol  41.23%
Anhydrous glycerine  8.24

Preparation

Add propylene glycol, Pluraflo, glycerine and ethanol to a clean vessel. While stirring, add ofloxacin. Stir unit a clear solution is obtained. Subsequently, add perfume and mix until uniform.

Example XVII

Composition for the Treatment of Glaucoma

| Component | % (w/w) |
| --- | --- |
| Timolol maleate | 0.25 |
| Vehicle[1] | 99.75 |

[1]Vehicle contains (w/w %):
Pluraflo 1220  92.73%
  (BASF Specialty Chemicals, Mount Olive, N.J.)
Ethanol  2.11%
Anhydrous glycerine  5.16

Preparation

Add glycerine, ethanol and Pluraflo to a clean vessel. Add Timolol. Cover tightly and stir until a clear solution is obtained.

Example XIII

Composition for the Treatment of Ulcers

| Component | % (w/w) |
| --- | --- |
| Omeprazole (Free Base) | 2.00 |
| Vehicle[1] | 95.89 |
| Sodium Metabisulfite | 0.10 |
| Disodium EDTA | 0.10 |
| Sodium Saccharin | 0.25 |
| Monoammonium Glycerizzinate | 0.11 |
| Acesulfame | 0.35 |
| Flavor | 1.20 |

[1]Vehicle contains (w/w %):
Pluronic F127  34.07%
  (BASF Specialty Chemicals, Mount Olive, N.J.)
Ethanol  10.43%
Water  13.32%
Propylene glycol  42.18%

Preparation

Add propylene glycol and poloxamer to a clean vessel (main mix). While stirring, heat the mixture as appropriate to sufficiently melt the poloxamer. Once a uniform solution is obtained remove from heat source and continue mixing. In a separate vessel (alcohol pre-mix) add alcohol, omeprazole base and monoammonium glycerizzinate and mix until uniform. In another vessel (water pre-mix), add water, EDTA , sodium saccharin, acesulfame and sodium metabisulfite. Mix until all materials are dissolved.

Add the alcohol containing premix to the main mixing vessel containing the poloxamer. Mix until uniform. While stirring, add the water containing premix to the main vessel and continue to mix until uniform. Subsequently, add desired flavor component and mix until uniform.

Example XIX

Composition for the Controlled Release of an Appetite Suppressant

| Component | % (w/w) |
|---|---|
| Phenylpropanolamine | 3.3 |
| Vehicle[1] | 96.5 |
| Sodium Metabisulfite | 0.10 |
| Disodium EDTA | 0.10 |

[1]Vehicle contains (w/w %):
Pluraflo 1220     70.12%
                          (BASF Specialty Chemicals, Mount Olive, N.J.)
Propylene glycol   11.27
Ethanol              2.26%
Anhydrous glycerine  16.35

Preparation

Add alcohol, propylene glycol, EDTA, sodium metabisulfite and phenylpropanolamine to a clean vessel and begin mixing. Subsequently, add, Pluraflo and glycerine to the vessel. Mix until uniform.

This liquid may be filled into hard gelatin capsules that are then banded to prevent leakage, or it may be used as the fill for a soft elastic gelatin capsule. One capsule is made to contain 0.75 ml of the liquid, and taken 3 times daily provides controlled release of the phenylpropanolamine active. After swallowing, the gelatin shell dissolves in the gastrointestinal tract and the liquid fill immediately transforms in to a slow dissolving gel that provides controlled release of the phenylpropanolamine.

Example XX

Composition for the Injection of an Analgesic

| Component | % (w/w) |
|---|---|
| Morphine Sulfate | 1.0 |
| Vehicle[1] | 99.0 |

[1]Vehicle contains (w/w %):
Pluraflo 1220     52.63%
                          (BASF Specialty Chemicals, Mount Olive, N.J.)
Propylene glycol   35.79%
Ethanol              3.16%
Anhydrous glycerine  8.42%

Preparation

Add propylene glycol, ethanol, glycerine and morphine sulfate into a clean vessel and begin mixing. Subsequently, add poloxamer (Pluraflo) and mix until uniform.

The composition provides pain relief when 1 mL is injected intramuscularly.

What is claimed is:

1. A pourable liquid vehicle comprising:
   (a) from about 26% to about 97% by weight of a polyoxyalkylene block copolymer;
   (b) from about 2% to about 70% by weight of a glycol; and
   (c) from about 1% to about 50% by weight of water;
wherein said vehicle is used to deliver compositions, materials, and substances to moistened surfaces and aqueous environments, wherein said vehicle has a viscosity value $\eta_f$ less than or equal to 7 pascal-seconds and a value T greater than or equal to about 1.3, and wherein said vehicle comprises weight ratios of the polyoxyalkylene block copolymer to the glycol of from about 1:0.16 to about 1:2.20, the polyoxalkylene block copolymer to the water of from about 1:0.10 to about 1:2.0, and the glycol to the water of from about 1:0.08 to about 1:4.25.

2. The pourable liquid vehicle according to claim 1 wherein the polyoxyalkylene block copolymer corresponds to the following structure:

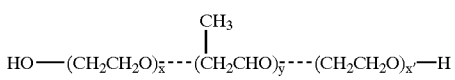

wherein x has a value from about 1 to about 130, y has a value from about 1 to about 72, and x' has a value from 0 to about 130, and wherein the polyoxyalkylene block copolymer has an average molecular weight of from about 3,000 to about 15,000.

3. The vehicle according to claim 2 comprising from about 27.8% to about 95% of the polyoxyalkylene block copolymer wherein said vehicle has a viscosity $\eta_f$ less than or equal to 2 pascal-seconds and value T is greater than or equal to about 2.

4. The vehicle according to claim 2 comprising from about 30% to about 90% of the polyoxyalkylene block copolymer wherein said vehicle has a viscosity $\eta_f$ less than or equal to 2 pascal-seconds and value T is greater than or equal to about 5.

5. The vehicle according to claim 1 comprising from about 10% to about 70% by weight of the glycol.

6. The vehicle according to claim 5 wherein said glycol is selected from the group consisting of monosaccharides, disaccharides, ribose, glycerin, sorbitol, xylitol, inositol, propylene glycol, galactose, mannose, xylose, rhamnose, glutaraldehyde, invert sugars, honey, mannitol, polyethylene glycol, glycerol, and mixtures thereof.

7. The vehical according to claim 1 comprising from about 1% to about 46% by weight of water.

8. The vehicle according to claim 2 comprising:
   (a) from about 26% to about 65% by weight of the polyoxyalkylene block copolymer wherein x is equal to 100, y is equal to 70, and x' is equal to 100, and the average molecular weight of the polyoxyalkylene block copolymer is about 12,600;
   (b) from about 22% to about 38% by weight of the glycol; and
   (c) from about 8% to about 45% by weight of water.

9. The vehicle according to claim 2 comprising:
   (a) from about 25% to about 50% by weight of the polyoxyalkylene block copolymer wherein x is equal to 37, y is equal to 58, and x' is equal to 37, and the average molecular weight of the polyoxyalkylene block copolymer is about 6,500;

(b) from about 45% to about 65% by weight of the glycol; and (c) from about 5% to about 20% by weight of water.

10. The vehicle according to claim 2 comprising:

(a) from about 52% to about 60% by weight of the polyoxyalkylene block copolymer wherein x is equal to 128, y is equal to 58, and x' is equal to 128, and the average molecular weight of the polyoxyalkylene block copolymer is about 14,600;

(b) from about 20% to about 25% by w.eight of the glycol; and (c) from about 17% to about 27% by weight of water.

11. The vehicle according to claim 2 comprising:

(a) from about 37% to about 77% by weight of the polyoxyalkylene block copolymer wherein x is equal to 37, y is equal to 58, and x' is equal to 37, and the average molecular weight of the polyoxyalkylene block copolymer is about 6,500;

(b) from about 12% to about 28% by weight of the glycol; and (c) from about 10% to about 45% by weight of water.

12. The vehicle according to claim 2 comprising:

(a) from about 26% to about 49% by weight of the polyoxyalkylene block copolymer wherein x is equal to 100, y is equal to 70, and x' is equal to 100, and the average molecular weight of the polyoxyalkylene block copolymer is about 12,600;

(b) from about 30% to about 68% by weight of the glycol;

(c) from about 2% to about 12 % by weight of ethanol; and (d) from about 7% to about 40% by weight of water.

13. A method for delivery of pharmacologically active agents to mammals by administering the pourable liquid vehicle of claim 1 to a moistened site on or in said mammal wherein said vehicle has a viscosity $\eta_f$ less than or equal to 7 pascal-seconds and a value T greater than or equal to about 1.4.

14. The vehicle according to claim 1 wherein said compositions, materials, and substances are dietary compositions, pharmacologically active agents, or antimicrobials.

15. The vehicle according to claim 9 wherein the glycol is propylene glycol.

16. The vehicle according to claim 12 wherein the glycol is propylene glycol.

17. The vehicle according to claim 6 wherein the said vehicle further comprises from about 2% to about 70% by weight of ethanol, wherein said vehicle comprises weight ratios of the polyoxyalkylene block copolymer to the ethanol of from about 1:0.16 to about 1:2.2, the polyoxyalkylene block copolymer to the water of from about 1:0.10 to about 1:2.0, and the ethanol to the water of from about 1:0.08 to about 1:4.25.

18. A pourable liquid vehicle comprising:

(a) from about 26% to about 100% by weight of a polyoxyalkylene block copolymer; and (b) from 0% to about 70% by weight of a glycol;

wherein said vehicle is used to deliver compositions, materials, and substances to moistened surfaces and aqueous environments, and wherein said vehicle has a viscosity value $\eta_f$ less than or equal to 7 pascal-seconds and a value T greater than or equal to about 1.3.

19. The pourable liquid vehicle according to claim 18 wherein the polyoxyakylene block copolymer corresponds to the following structure:

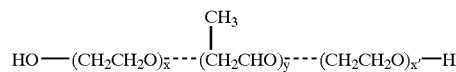

wherein x has a value from about 1 to about 130, y has a value from about 1 to about 72, and x' has a value from 0 to about 130, and wherein the polyoxyalkylene block copolymer has an average molecular weight of from about 3,000 to about 15,000.

20. The pourable liquid vehicle according to claim 18 wherein the glycol is selected from the group consisting of monosaccharides, disaccharides, ribose, glycerin, sorbitol, xylitol, inositol, propylene glycol, galactose, mannose, xylose, rhamnose, glutaraldehyde, invert sugars, honey, mannitol, polyethylene glycol, glycerol, and mixtures thereof.

21. The pourable liquid vehicle according to claim 20 wherein said vehicle further comprises from 0% to about 70% by weight of ethanol.

22. A pourable liquid vehicle comprising:

(a) from about 26% to about 97% by weight of a polyoxyalkylene block copolymer;

(b) from about 2% to about 70% by weight of ethanol; and (c) from about 1% to about 50% by weight of water;

wherein said vehicle is used to deliver compositions, materials, and substances to moistened surfaces and aqueous environments, wherein said vehicle has a viscosity value $\eta_f$ less than or equal to 7 pascal-seconds and a value T greater than or equal to about 1.3, and wherein said vehicle comprises weight ratios of the polyoxyalkylene block copolymer to the ethanol of from about 1:0.16 to about 1:2.2, the polyoxyalkylene block copolymer to the water of from about 1:0.10 to about 1:2.0, and the ethanol to the water of from about 1:0.08 to about 1:4.25.

23. The pourable liquid vehicle according to claim 22 wherein the polyoxyalkylene block copolymer corresponds to the following structure:

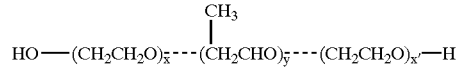

wherein x has a value from about 1 to about 130, y has a value from about 1 to about 72, and x' has a value from 0 to about 130, and wherein the polyoxyalkylene block copolymer has an average molecular weight of from about 3000 to about 15,000.

24. The vehicle according to claim 23 comprising:

(a) from about 26% to about 65% by weight of the polyoxyalkylene block copolymer wherein x is equal to 100, y is equal to 70, and x' is equal to 100, and the average molecular weight of the polyoxyalkylene block copolymer is about 12,600;

(b) from about 22% to about 38% by weight of the ethanol; and (c) from about 8% to about 45% by weight of water.

25. The vehicle according to claim 23 comprising:

(a) from about 52% to about 60% by weight of the polyoxyalkylene block copolymer wherein x is equal to 128, y is equal to 58, and x' is equal to 128, and the average molecular weight of the polyoxyalkylene block copolymer is about 14,600;

(b) from about 20% to about 25% by weight of the ethanol; and (c) from about 17% to about 27% by weight of water.

26. The vehicle according to claim 23 comprising:
(a) from about 37% to about 77% by weight of the polyoxyalkylene block copolymer wherein x is equal to 37, y is equal to 58, and x' is equal to 37, and the average molecular weight of the polyoxyalkylene block copolymer is about 6,500;
(b) from about 12% to about 28% by weight of the ethanol; and
(c) from about 10% to about 45% by weight of water.

27. A method for delivery of pharmacologically active agents to mammals by administering the pourable liquid vehicle of claim 22 to a moistened site on or in said mammal wherein said vehicle has a viscosity $\eta_f$ less than or equal to 7 pascal-seconds and a value T greater than or equal to about 1.4.

* * * * *